(12) United States Patent
Toda

(10) Patent No.: US 6,340,347 B1
(45) Date of Patent: Jan. 22, 2002

(54) VIBRATION DISPLACEMENT SENSING DEVICE

(76) Inventor: Kohji Toda, 1-49-18 Futaba, Yokosuka (JP), 239-0814

( * ) Notice: Subject to any disclaimer, the term of this patent is extended or adjusted under 35 U.S.C. 154(b) by 0 days.

(21) Appl. No.: 09/557,056

(22) Filed: Apr. 21, 2000

(51) Int. Cl.⁷ .................................................. A61B 8/00
(52) U.S. Cl. ............................ 600/438; 600/459; 73/570
(58) Field of Search .................................. 600/437, 438, 600/459; 73/61.45, 61.75, 61.78, 570, 573–575, 579, 584, 644, 649, DIG. 4

(56) References Cited

U.S. PATENT DOCUMENTS

| | | | | |
|---|---|---|---|---|
| 4,691,714 A | * | 9/1987 | Wong et al. ................. | 600/551 |
| 4,905,701 A | * | 3/1990 | Cornelius .................... | 600/437 |
| 5,143,072 A | * | 9/1992 | Kantorvich et al. ......... | 600/437 |
| 5,305,758 A | * | 4/1994 | Dietz et al. .................. | 600/465 |
| 5,400,788 A | * | 3/1995 | Dias et al. ................... | 600/459 |
| 5,766,137 A | * | 6/1998 | Omato ......................... | 600/587 |
| 6,142,948 A | * | 11/2000 | Toda ............................ | 600/459 |
| 6,144,332 A | * | 11/2000 | Reindl et al. ................. | 342/42 |

* cited by examiner

Primary Examiner—Francis J. Jaworski

(57) ABSTRACT

A vibration displacement sensing device comprises a piezoelectric substrate, an input interdigital transducer, a first output interdigital transducer, a second output interdigital transducer, and a signal analyzer. All the input-, the first output-, and the second output interdigital transducers are formed on one end surface of the piezoelectric substrate. If an input electric signal is applied to the input interdigital transducer, an elastic wave is excited in the piezoelectric substrate. A leaky component of the elastic wave is radiated effectively in the form of a longitudinal wave toward a first material located inside a second material which is in contact with the other end surface of the piezoelectric substrate and has an acoustic impedance different from that of the first material. The longitudinal wave is reflected by the first material. A reflected longitudinal wave is detected at the first output interdigital transducer as a first delayed electric signal. A non-leaky component of the elastic wave is detected at the second output interdigital transducer as a second delayed electric signal. A vibration displacement caused by the first material is sensed by the signal analyzer from a difference between the first- and second delayed electric signals.

8 Claims, 8 Drawing Sheets blood vessel   skin
cellular tissue   gel solution

VIBRATION DISPLACEMENT SENSING DEVICE

BACKGROUND OF THE INVENTION

1. Field of the Invention

The present invention relates to a device for sensing a vibration displacement generated by a first material located inside a second material, which has an acoustic impedance different from that of the first material, by means of using a sensing assembly composed of a piezoelectric substrate, an input interdigital transducer, a first- and a second output interdigital transducers.

2. Description of the Prior Art

There are two types, that is, a touch-type and an untouch-type, of conventional devices for sensing a vibration displacement. For example, an electric micrometer for measuring a minute displacement, a linear scale for a large displacement, and a rotary encoder for a rotation displacement belong to the touch-type of device. The electric micrometer and the linear scale is used as, for example, a reference for measuring the length of a material. The rotary encoder is used for controlling a rotation velocity or a rotation frequency of a rotatory material. The touch-type of device has some problems on measurement accuracy, response time, difficulty in use, durability and manufacturing. On the other hand, for example, a laser-type sensor and an electroacoustic-type sensor belong to the untouch-type of device. The laser-type sensor including a semiconductor position-sensing device is mainly used for measuring a vibration displacement along the direction vertical to the laser beam applied to a material. The laser-type sensor has a defect that the longer the length of the laser beam, the lower the measurement accuracy because of flickering of the laser beam itself. In addition, the use of the laser-type sensor is impossible for the measurement in opaque media. The electroacoustic-type sensor is used for measuring the vibration displacement in a material near a terminal of a pipe. The electroacoustic-type sensor is easy to be affected by a change in circumstances, and has some problems on measurement accuracy, and so on.

SUMMARY OF THE INVENTION

An object of the present invention is to provide a vibration displacement sensing device capable of sensing a vibration displacement generated by a first material located inside a second material, which has an acoustic impedance different from that of the first material, with a high sensitivity.

Another object of the present invention is to provide a vibration displacement sensing device capable of operating at a high frequency.

Another object of the present invention is to provide a vibration displacement sensing device capable of transducing a vibration displacement to an electric signal.

Another object of the present invention is to provide a vibration displacement sensing device excellent in measurement accuracy, response time, durability, manufacturing.

Another object of the present invention is to provide a vibration displacement sensing device which is not affected by a change in circumstances, for example, a change in temperature.

A still other object of the present invention is to provide a vibration displacement sensing device easy in use and having a small size which is very light in weight and has a simple structure.

According to one aspect of the present invention there is provided a vibration displacement sensing device comprising a piezoelectric substrate having two end surfaces an input interdigital transducer, a first output interdigital transducer, a second output interdigital transducer, and a signal analyzer. All the input-, the first output-, and the second output interdigital transducers are formed on one end surface of the piezoelectric substrate.

If an input electric signal is applied to the input interdigital transducer, an elastic wave is excited in the piezoelectric substrate. A leaky component of the elastic wave is radiated effectively in the form of a longitudinal wave toward a first material located inside a second material which is in contact with the other end surface of the piezoelectric substrate and has an acoustic impedance different from that of the first material. The longitudinal wave is reflected by the first material. A reflected longitudinal wave is detected at the first output interdigital transducer as a first delayed electric signal. A non-leaky component of the elastic wave is detected at the second output interdigital transducer as a second delayed electric signal. A vibration displacement caused by the first material is sensed by the signal analyzer from a difference between the first- and second delayed electric signals.

According to another aspect of the present invention there is provided a cellular tissue in contact with the other end surface of the piezoelectric substrate, and a blood vessel located in the cellular tissue. In this case, the blood vessel reflects the longitudinal wave.

According to another aspect of the present invention there is provided an amplifier connected between the input interdigital transducer and the second output interdigital transducer. A part of the second delayed electric signal is amplified via the amplifier, and is fed back as the input electric signal again. Thus, the input interdigital transducer, the second output interdigital transducer and the amplifier form a self-oscillation type of delay-line oscillator.

According to another aspect of the present invention there is provided an amplifier connected between the input interdigital transducer and the first output interdigital transducer. A part of the first delayed electric signal is amplified via the amplifier, and is fed back as the input electric signal again. Thus, the input interdigital transducer, the first output interdigital transducer and the amplifier form a self-oscillation type of delay-line oscillator.

According to another aspect of the present invention there is provided a signal analyzer comprising a phase comparator, which compares an acoustic phase delay of the first delayed electric signal with that of the second delayed electric signal. Thus, a vibration displacement caused by the first material is sensed by the signal analyzer in terms of a phase difference between the firsthand second delayed electric signals.

According to another aspect of the present invention there are provided an input-, a first output-, and a second output interdigital transducers having an arch-shape, respectively, and arranged to have one concentric center.

According to other aspect of the present invention there is provided a piezoelectric substrate made of a piezoelectric ceramic thin plate, of which the polarization axis is parallel to the thickness direction thereof.

According to a further aspect of the present invention there is provided a piezoelectric polymer thin plate.

BRIEF DESCRIPTION OF THE DRAWINGS

Other features and advantages of the invention will be clarified from the following description with reference to the attached drawings.

DETAILED DESCRIPTION OF THE PRESENTLY PREFERRED EXEMPLARY EMBODIMENTS

Figure 1:
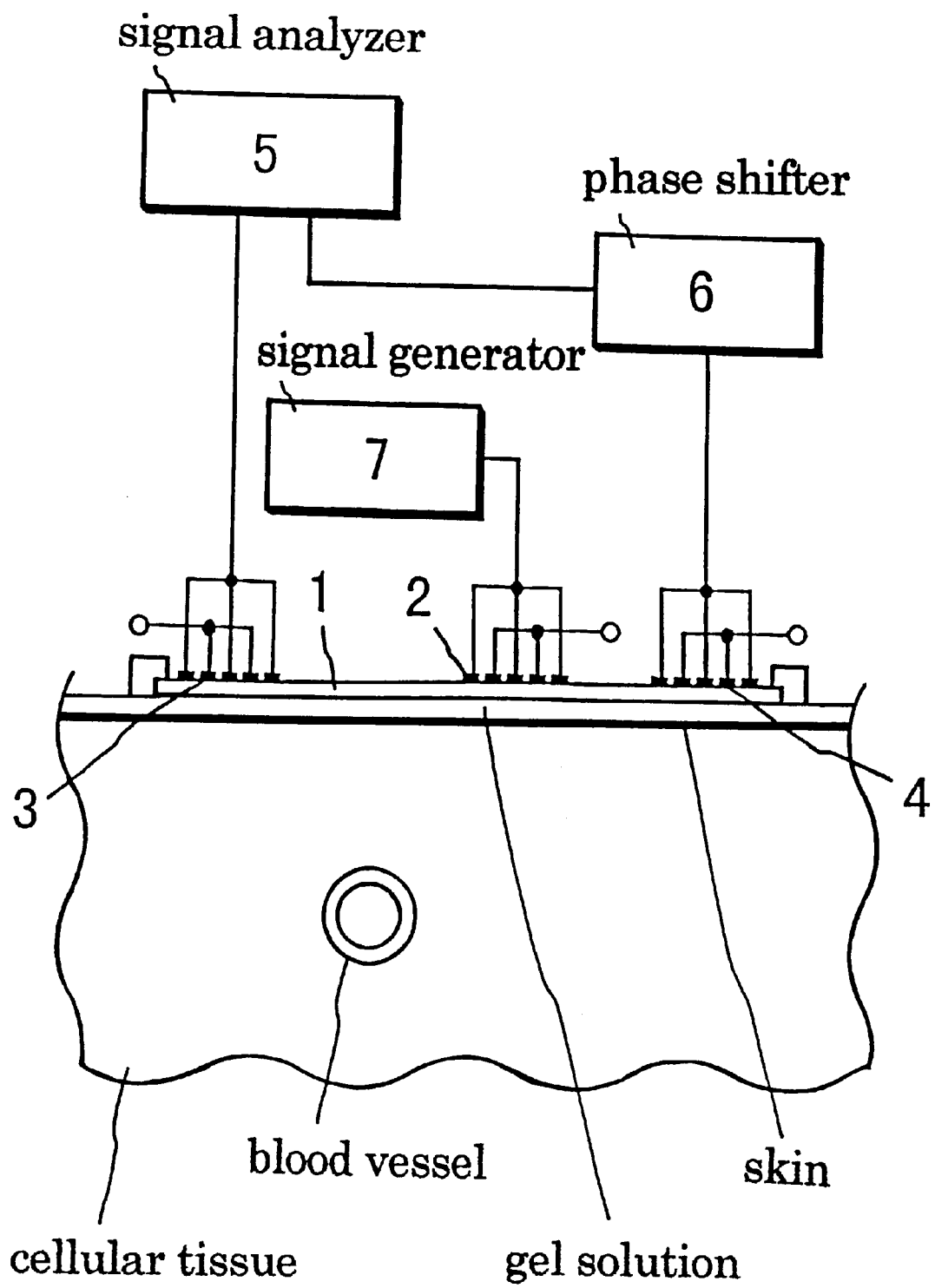
FIG. 1 shows a schematic illustration of a vibration displacement sensing device according to a first embodiment of the present invention.

FIG. 1 shows a schematic illustration of a vibration displacement sensing device according to a first embodiment of the present invention. The vibration displacement sensing device comprises piezoelectric substrate 1, input interdigital transducer 2, first output interdigital transducer 3, second output interdigital transducer 4, signal analyzer 5, phase shifter 6, and signal generator 7. Piezoelectric substrate 1 is made of a piezoelectric ceramic thin plate. It is possible to use a piezoelectric polymer plate as piezoelectric substrate 1. Input interdigital transducer 2, first output interdigital transducer 3 and second output interdigital transducer 4, having an arch-shape and made of an aluminum thin film, respectively, are formed on one end surface of piezoelectric substrate 1. Piezoelectric substrate 1, input interdigital transducer 2, first output interdigital transducer 3 and second output interdigital transducer 4 form a sensing assembly. Signal analyzer 5 is made of a phase comparator. When sensing a vibration displacement generated by a first material located inside a second material, the other end surface of piezoelectric substrate 1 is kept in contact with the second material, which has an acoustic impedance different from that of the first material. Thus, when sensing, for example, a person's pulse, that is a vibration displacement generated by a blood vessel in a cellular tissue, the other end surface of piezoelectric substrate 1 is kept in contact with, for example, a human wrist. In addition, it is better to spread a gel solution on a skin near the blood vessel in the cellular tissue. Thus, the vibration displacement sensing device in FIG. 1 has a small size which is very light in weight and has a simple structure.

Figure 2:
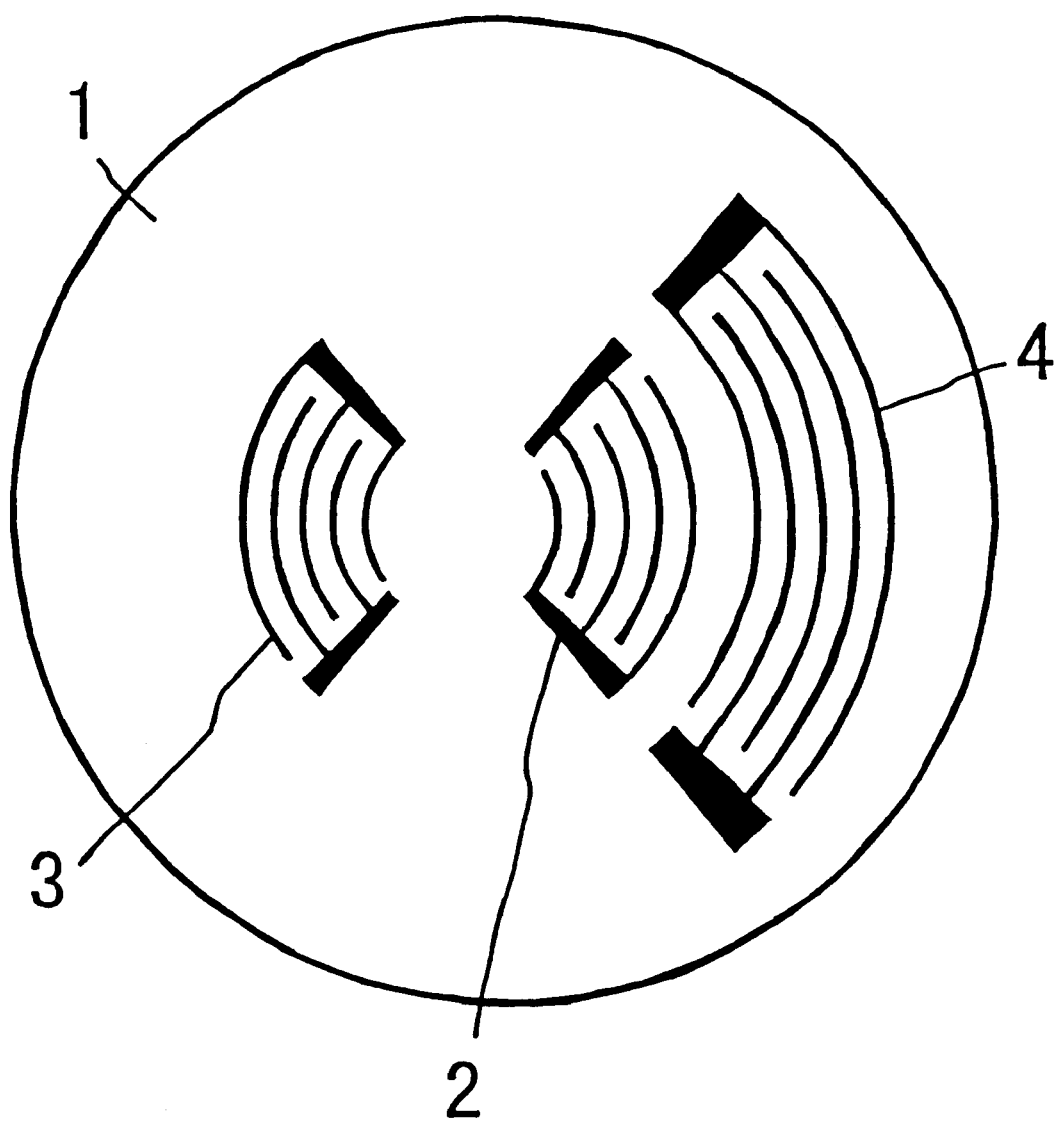
FIG. 2 shows a top plan view of the sensing assembly shown in FIG. 1.

FIG. 2 shows a top plan view of the sensing assembly shown in FIG. 1. The separation length between input interdigital transducer 2 and first output interdigital transducer 3 is 6 mm. Input interdigital transducer 2, first output interdigital transducer 3 and second output interdigital transducer 4 are arranged to have one concentric center, and have an aperture angle of 45°, an interdigital periodicity of 340 $\mu$m and 5 finger pairs, respectively. When sensing a person's pulse, the other end surface of piezoelectric substrate 1 is put on the gel solution such that the concentric center is located just over the blood vessel.

Figure 3:
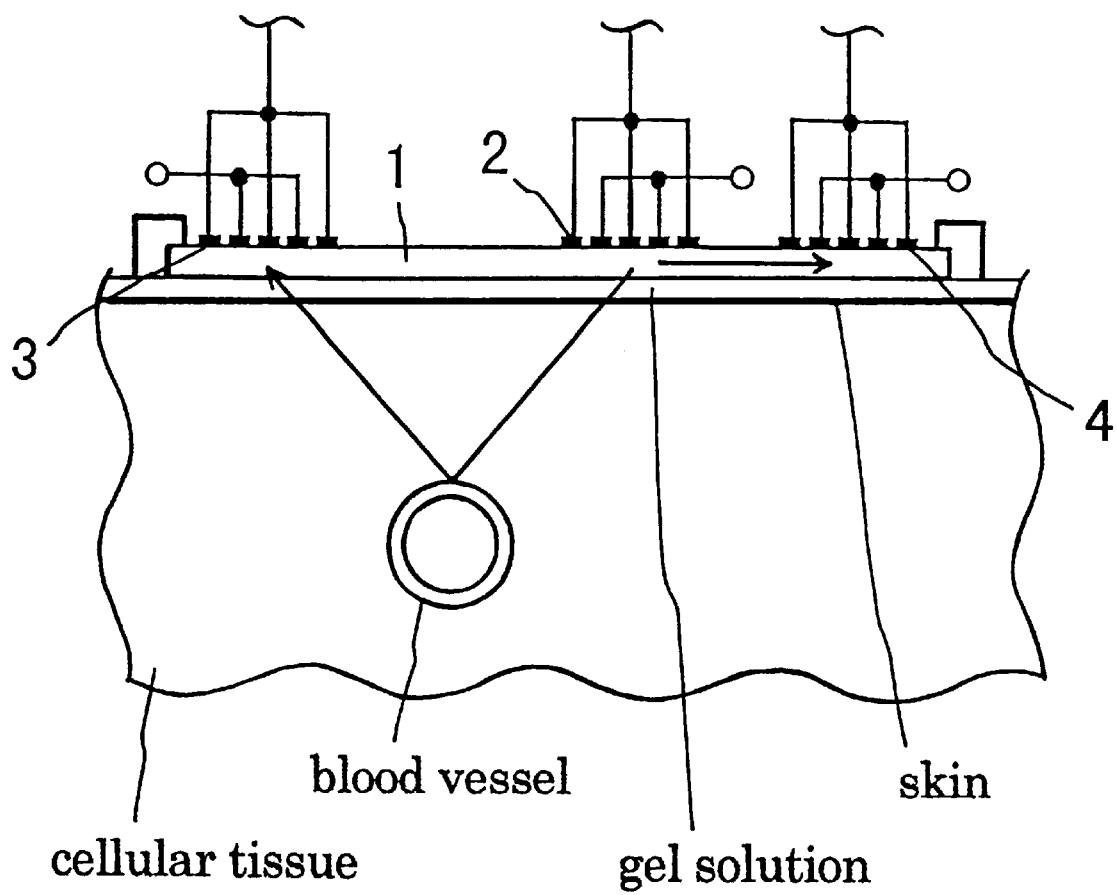
FIG. 3 shows an illustration exhibiting a path of the longitudinal wave traveling in the cellular tissue by an arrow.

In the vibration displacement sensing device in FIG. 1, if an input electric signal, with a frequency approximately corresponding to an interdigital periodicity of input interdigital transducer 2, is applied from signal generator 7 to input interdigital transducer 2, an elastic wave is excited in piezoelectric substrate 1. Because piezoelectric substrate 1 is made of a piezoelectric ceramic, and in addition, the polarization axis thereof is parallel to the thickness direction thereof, the elastic wave is excited in piezoelectric substrate 1 effectively. When sensing a person's pulse, a leaky component of the elastic wave having the wavelength approximately equivalent to the interdigital periodicity is radiated effectively toward a blood vessel in a cellular tissue in the form of a longitudinal wave, in other words, a mode conversion from the leaky component of the elastic wave to the longitudinal wave occurs. Such effective radiation is owing to the arch-shape of input interdigital transducer 2, which enables an ultrasound beam to go along a slant direction to the other end surface of piezoelectric substrate 1. The longitudinal wave is reflected by the blood vessel in the cellular tissue. A reflected longitudinal wave is detected at first output interdigital transducer 3 as a first delayed electric signal with a frequency approximately corresponding to the interdigital periodicity. Such detection of the first delayed electric signal is due to the arch-shape of first output interdigital transducer 3, which can detect an ultrasound beam from a slant direction to the other end surface of piezoelectric substrate 1. On the other hand, a non-leaky component of the elastic wave is transmitted to second output interdigital transducer 4, and detected at second output interdigital transducer 4 as a second delayed electric signal. Then, an acoustic phase delay of the first delayed electric signal is compared with that of the second delayed electric signal at signal analyzer 5. In this time, the phase of the first delayed electric signal is controlled to be coincident with that of the second delayed electric signal by phase shifter 6, when sensing no vibration displacement. FIG. 3 shows an illustration exhibiting a path of the longitudinal wave traveling in the cellular tissue by an arrow. Because the blood vessel vibrates continuously, a length of traveling path of the longitudinal wave is changed. A change in length of traveling path brings about a difference between an acoustic phase delay of the first delayed electric signal and that of the second delayed electric signal. Thus, a vibration displacement generated by the blood vessel can be sensed by signal analyzer 5 in terms of a phase difference. In addition, such a sensing system as comparing the two phases is not affected by a temperature change. Thus, it is possible to measure, for example, a person's pulse a minute with a high sensitivity.

Figure 4:
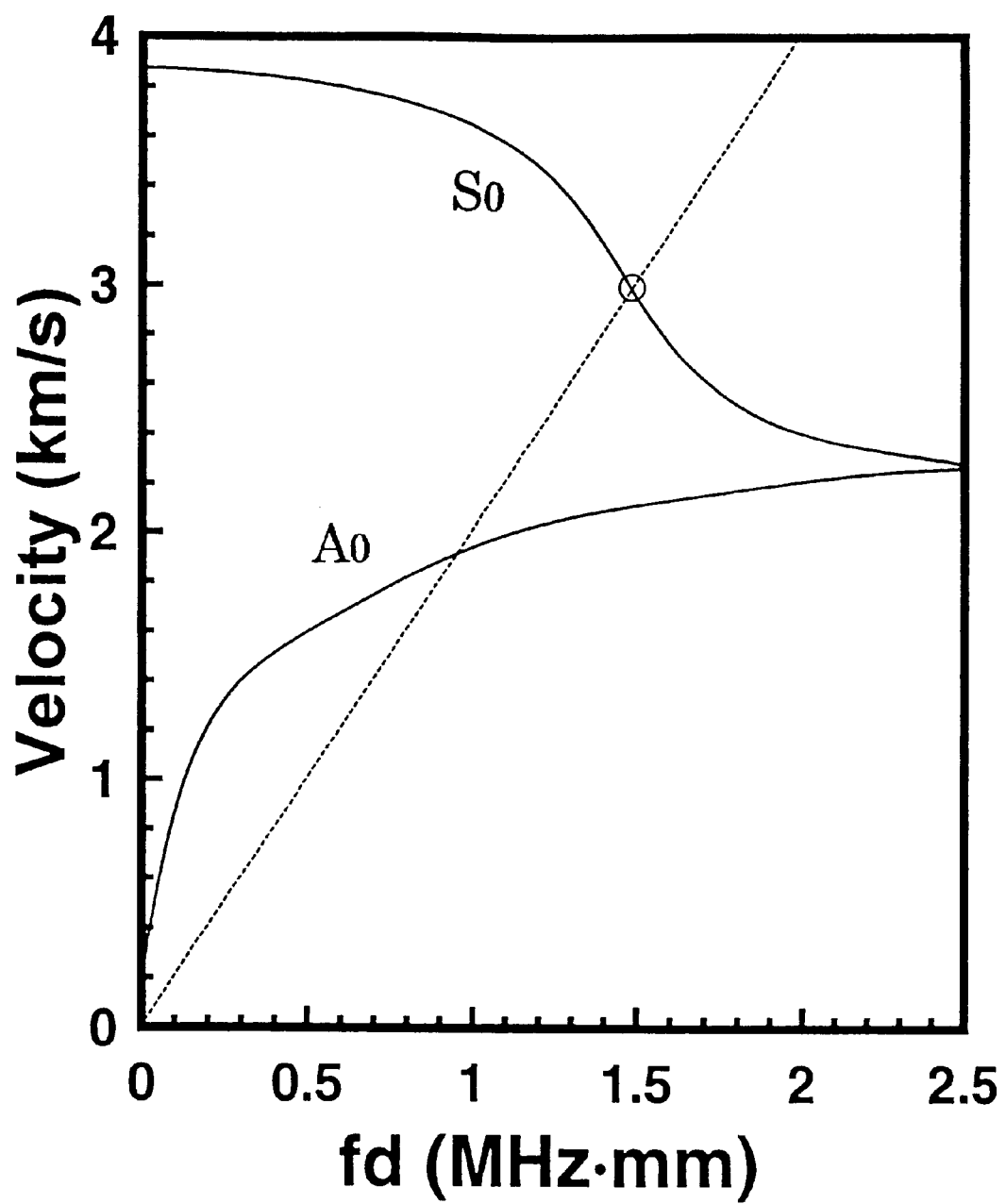
FIG. 4 shows a relationship between the phase velocity of an elastic wave for the $A_0$ mode and the $S_0$ mode in piezoelectric substrate 1, and the product fd.

FIG. 4 shows a relationship between the phase velocity of an elastic wave for the $A_0$ mode and the $S_0$ mode in piezoelectric substrate 1, and the product fd, where f is a frequency of the elastic wave and d is a thickness of piezoelectric substrate 1. Piezoelectric substrate 1 has a shear wave velocity of 2,450 m/s and a longitudinal wave velocity of 4,390 m/s.

Figure 5:
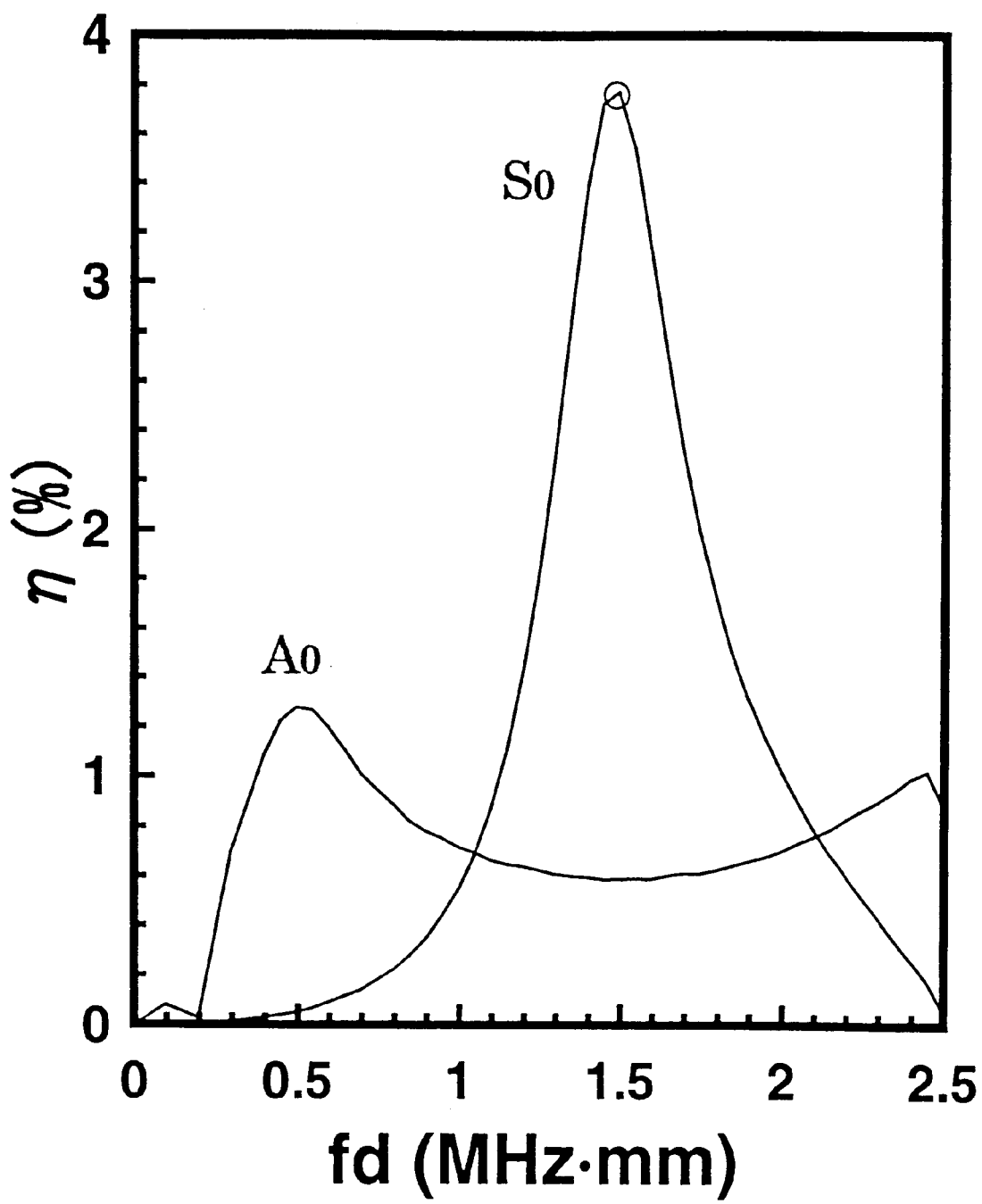
FIG. 5 shows a relationship between the calculated transducer efficiency $\eta$ for a longitudinal wave radiation into water, and the product fd.

FIG. 5 shows a relationship between the calculated transducer efficiency $\eta$ for a longitudinal wave radiation into water, and the product fd. It should be noted that the $S_0$ mode curve has the highest peak at around 1.5 MHz•mm, that is the most appropriate operation condition.

Figure 6:
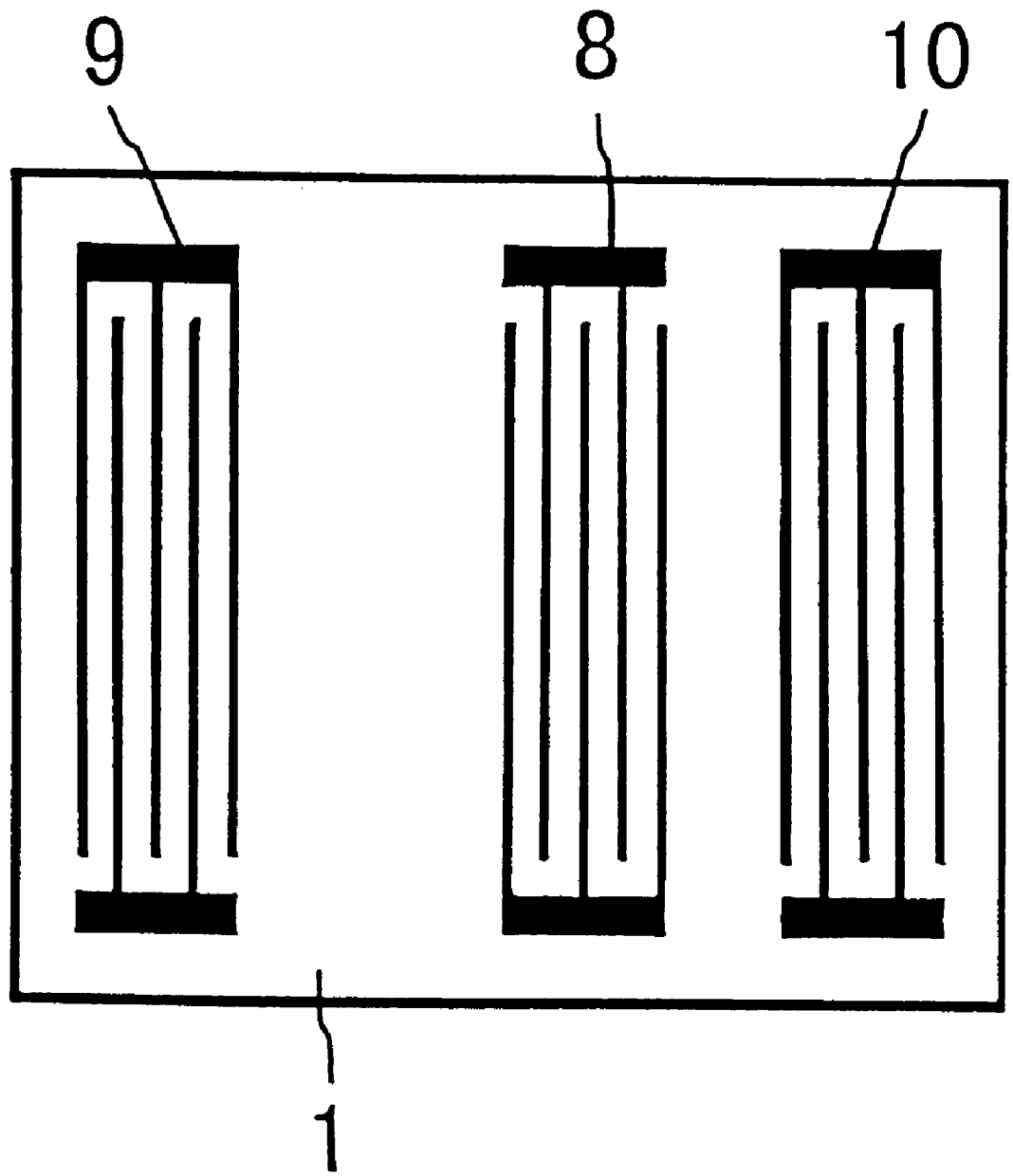
FIG. 6 shows a top plan view of another sensing assembly used in place of the assembly in FIG. 2.
Figure 7:
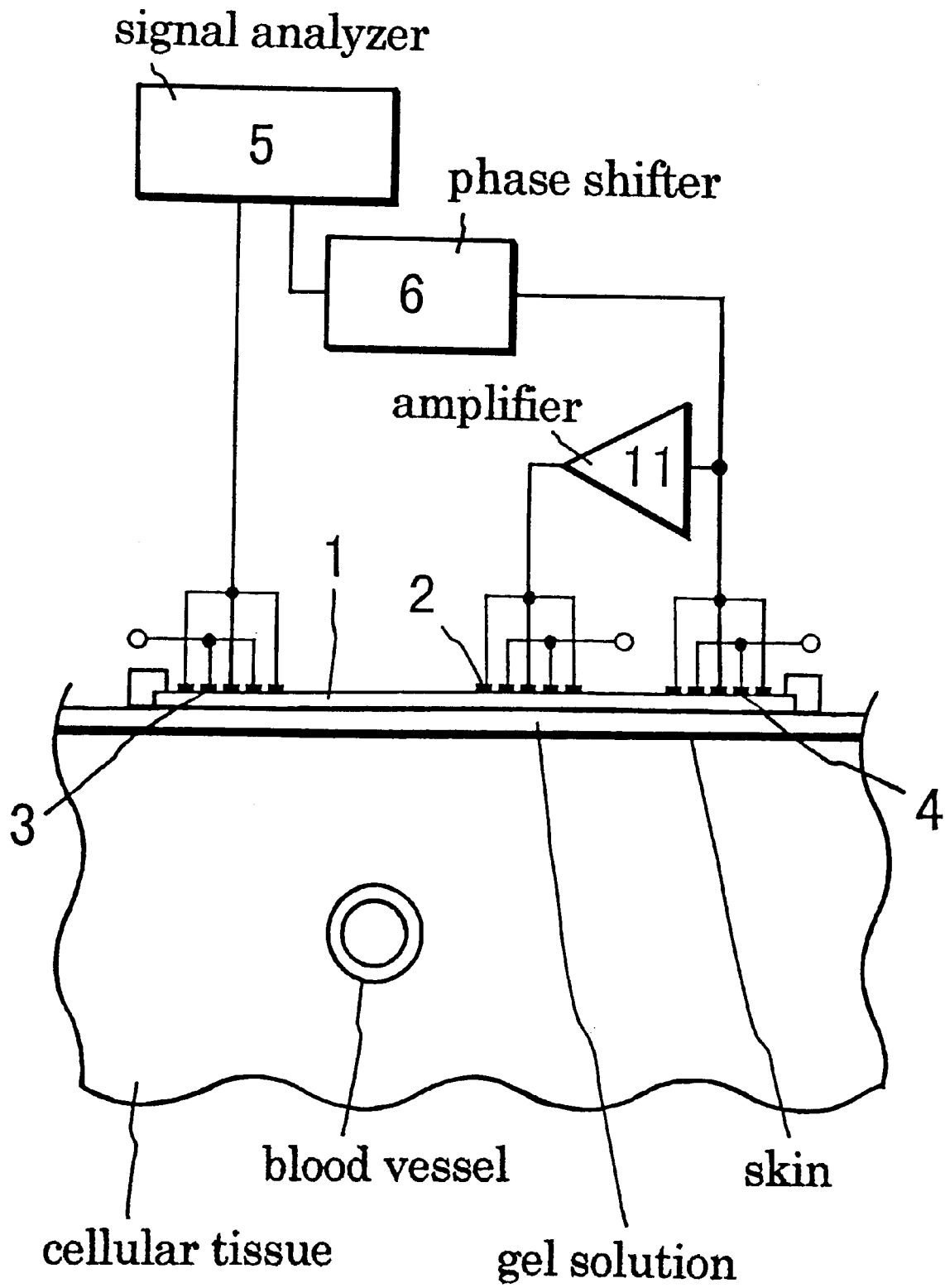
FIG. 7 shows a schematic illustration of a vibration displacement sensing device according to a second embodiment of the present invention.

FIG. 6 shows a top plan view of another sensing assembly used in place of the assembly in FIG. 2. The sensing assembly in FIG. 6 comprises piezoelectric substrate 1, input interdigital transducer 8, first output interdigital transducer 9 and second output interdigital transducer 10, and has the same function as FIG. 2. FIG. 7 shows a schematic illustration of a vibration displacement sensing device according to a second embodiment of the present invention. The vibration displacement sensing device comprises piezoelectric substrate 1, input interdigital transducer 2, first output interdigital transducer 3, second output interdigital transducer 4, signal analyzer 5, phase shifter 6, and amplifier 11, which is connected between input interdigital transducer 2 and second output interdigital transducer 4.

In the vibration displacement sensing device in FIG. 7, if an input electric signal is applied to input interdigital transducer 2, an elastic wave is excited in piezoelectric substrate 1. A leaky component of the elastic wave is radiated effectively in the form of a longitudinal wave into the cellular tissue, and then, reflected by the blood vessel. A reflected longitudinal wave is detected at first output interdigital transducer 3 as a first delayed electric signal. A non-leaky component of the elastic wave is transmitted to second output interdigital transducer 4, and detected at second output interdigital transducer 4 as a second delayed electric signal. A part of the second delayed electric signal is amplified via amplifier 11, and is fed back as the input electric signal again. Thus, input interdigital transducer 2, second output interdigital transducer 4 and amplifier 11 form a self-oscillation type of delay-line oscillator. A remaining part of the second delayed electric signal is transmitted to signal analyzer 5, where an acoustic phase delay of the first delayed electric signal is compared with that of the second delayed electric signal. In this time, the phase of the first delayed electric signal is controlled to be coincident with that of the second delayed electric signal by phase shifter 6, when sensing no vibration displacement. Thus, a vibration displacement generated by the blood vessel can be sensed by signal analyzer 5 in terms of the phase difference between the first- and second delayed electric signals with a high sensitivity.

Figure 8:
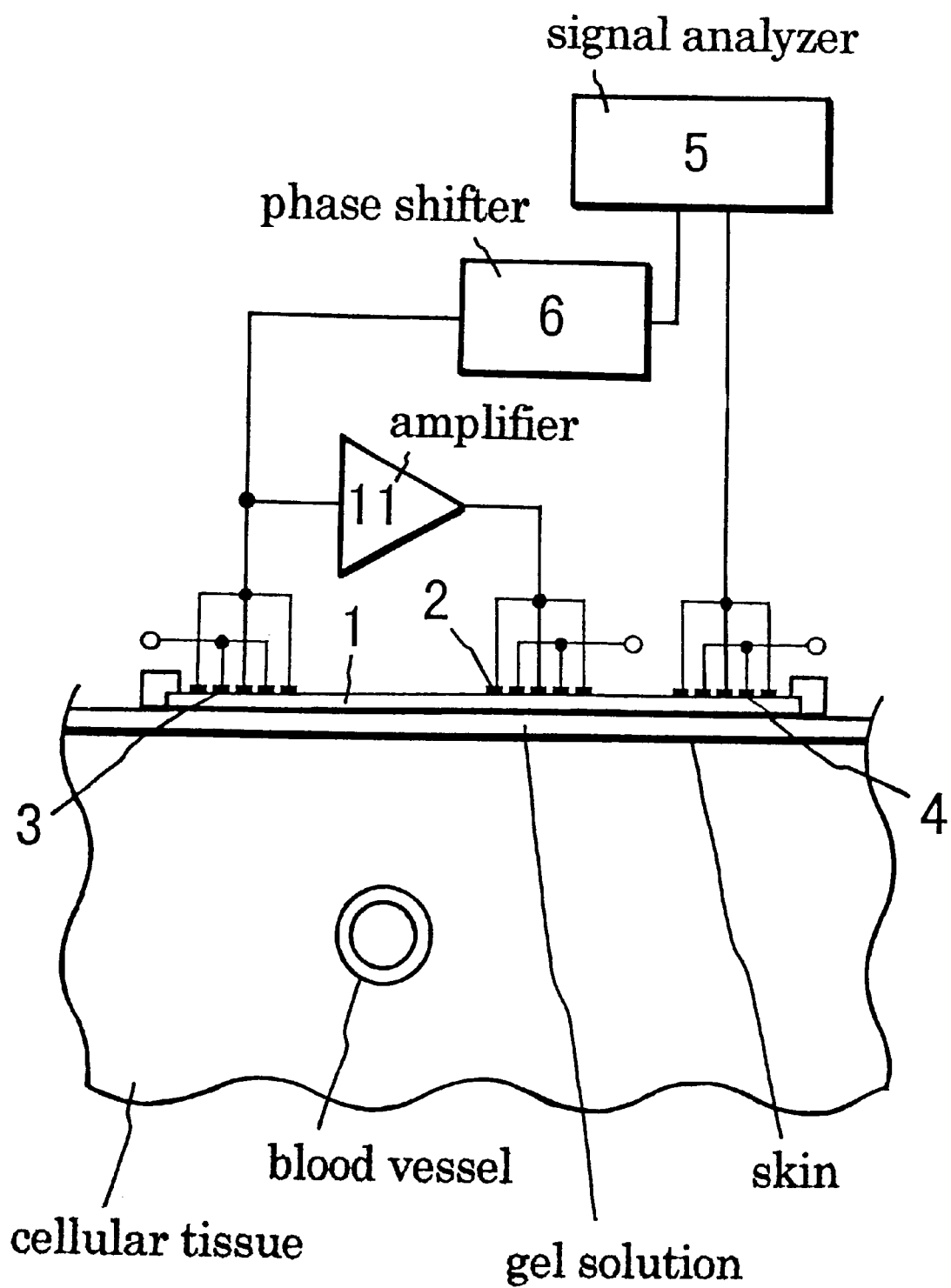
FIG. 8 shows a schematic illustration of a vibration displacement sensing device according to a third embodiment of the present invention.

FIG. 8 shows a schematic illustration of a vibration displacement sensing device according to a third embodiment of the present invention. The vibration displacement sensing device has the same construction as FIG. 7, except for a position of amplifier 11, which is connected between input interdigital transducer 2 and first output interdigital transducer 3.

In the vibration displacement sensing device in FIG. 8, a part of a first delayed electric signal detected at first output interdigital transducer 3 is amplified via amplifier 11, and is fed back as the input electric signal again. Thus, input interdigital transducer 2, first output interdigital transducer 3 and amplifier 11 form a self-oscillation type of delay-line oscillator. A vibration displacement generated by the blood vessel can be sensed by signal analyzer 5 in terms of the phase difference between the first- and second delayed electric signals with a high sensitivity.

While this invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

What is claimed is:

1. A vibration displacement sensing device comprising:

a piezoelectric substrate having two end surfaces;

an input interdigital transducer;

a first output interdigital transducer;

a second output interdigital transducer, all said input-, said first output-, and said second output interdigital transducers being formed on one end surface of said piezoelectric substrate; and a signal analyzer, said piezoelectric substrate, said input interdigital transducer, said first- and second output interdigital transducers forming a sensing assembly, said input interdigital transducer receiving an input electric signal, exciting an elastic wave, composed of a leaky- and a non-leaky components, in said piezoelectric substrate, radiating said leaky component of said elastic wave in the form of a longitudinal wave toward a first material located inside a second material which has an acoustic impedance different from that of said first material and is in contact with the other end surface of said piezoelectric substrate, and making said first material reflect said longitudinal wave back, said first output interdigital transducer detecting a reflected longitudinal wave as a first delayed electric signal, said second output interdigital transducer detecting said non-leaky component of said elastic wave as a second delayed electric signal, said signal analyzer sensing a vibration displacement caused by said first material from a difference between said first- and second delayed electric signals.

2. A vibration displacement sensing device as defined in claim 1, wherein said second material is a cellular tissue, and said first material is a blood vessel.

3. A vibration displacement sensing device as defined in claim 1 further comprising an amplifier connected between said input interdigital transducer and said second output interdigital transducer, said amplifier amplifying said second delayed electric signal, and said input interdigital transducer, said second output interdigital transducer and said amplifier forming a delay-line oscillator.

4. A vibration displacement sensing device as defined in claim 1 further comprising an amplifier connected between said input interdigital transducer and said first output interdigital transducer, said amplifier amplifying said first delayed electric signal, and said input interdigital transducer, said first output interdigital transducer and said amplifier forming a delay-line oscillator.

5. A vibration displacement sensing device as defined in claim 1, wherein said signal analyzer comprises a phase comparator, which compares an acoustic phase delay of said first delayed electric signal with that of said second delayed electric signal, and senses said vibration displacement in terms of a phase difference between said first- and second delayed electric signals.

6. A vibration displacement sensing device as defined in claim 1, wherein all said input-, said first output-, and said second output interdigital transducers have an arch-shape, respectively, and are arranged to have one concentric center.

7. A vibration displacement sensing device as defined in claim 1, wherein said piezoelectric substrate is made of a piezoelectric ceramic thin plate, the polarization axis thereof being parallel to the thickness direction thereof.

8. A vibration displacement sensing device as defined in claim 1, wherein said piezoelectric substrate is made of a piezoelectric polymer thin plate.

* * * * *